D)(12) United States Patent
Bagaoisan et al.

(10) Patent No.: US 9,468,745 B2
(45) Date of Patent: Oct. 18, 2016

(54) APPARATUS AND METHODS FOR INFLATING AND DEFLATING BALLOON CATHETERS

(75) Inventors: Celso J. Bagaoisan, Union City, CA (US); Glen Gong, San Carlos, CA (US); Suresh Pai, Mountain View, CA (US); Scott Robert Sershen, Redwood City, CA (US)

(73) Assignee: SPOTLIGHT TECHNOLOGY PARTNERS LLC, Los Altos, CA (US)

( * ) Notice: Subject to any disclaimer, the term of this patent is extended or adjusted under 35 U.S.C. 154(b) by 1 day.

(21) Appl. No.: 13/978,230

(22) PCT Filed: Jan. 4, 2012

(86) PCT No.: PCT/US2012/020201
§ 371 (c)(1),
(2), (4) Date: Sep. 23, 2013

(87) PCT Pub. No.: WO2012/094403
PCT Pub. Date: Jul. 12, 2012

(65) Prior Publication Data
US 2014/0005630 A1 Jan. 2, 2014

Related U.S. Application Data

(60) Provisional application No. 61/430,082, filed on Jan. 5, 2011.

(51) Int. Cl.
*A61M 25/10* (2013.01)

(52) U.S. Cl.
CPC .... *A61M 25/10182* (2013.11); *A61M 25/1018* (2013.01); *A61M 25/10184* (2013.11)

(58) Field of Classification Search
CPC ............... A61M 25/10181; A61M 25/10182; A61M 25/10184; A61M 25/10187; A61M 25/1018
USPC ....................... 604/97.01–97.03, 99.01–99.04
See application file for complete search history.

(56) References Cited

U.S. PATENT DOCUMENTS

| | | | |
|---|---|---|---|
| 3,985,122 A | 10/1976 | Topham | |
| 4,476,866 A * | 10/1984 | Chin | ............................. 606/194 |
| 4,743,230 A | 5/1988 | Nordquest | |
| 4,758,223 A | 7/1988 | Rydell | |
| 4,808,165 A * | 2/1989 | Carr | ........................... 604/97.02 |
| 4,832,692 A | 5/1989 | Box et al. | |
| 5,047,015 A | 9/1991 | Foote et al. | |
| 5,057,078 A | 10/1991 | Foote et al. | |
| 5,209,732 A | 5/1993 | Lampropoulos et al. | |
| 5,215,536 A | 6/1993 | Lampropoulos et al. | |
| 5,507,727 A | 4/1996 | Crainich | |
| 5,993,416 A | 11/1999 | Choh et al. | |
| 7,530,970 B2 | 5/2009 | McArthur et al. | |
| 2010/0211007 A1 | 8/2010 | Lesch, Jr. et al. | |

FOREIGN PATENT DOCUMENTS

WO 2010/096294 8/2010

\* cited by examiner

*Primary Examiner* — Theodore Stigell
(74) *Attorney, Agent, or Firm* — Edward J. Baba; Khin K. Chin; Bozicevic, Field & Francis LLP

(57) ABSTRACT

Among the various embodiments, objects and features of the present invention may generally be noted an inflation/deflation syringe that enables one-handed operation to inflate a medical device to a given pressure or volume and one-handed operation to deflate said medical device.

23 Claims, 12 Drawing Sheets

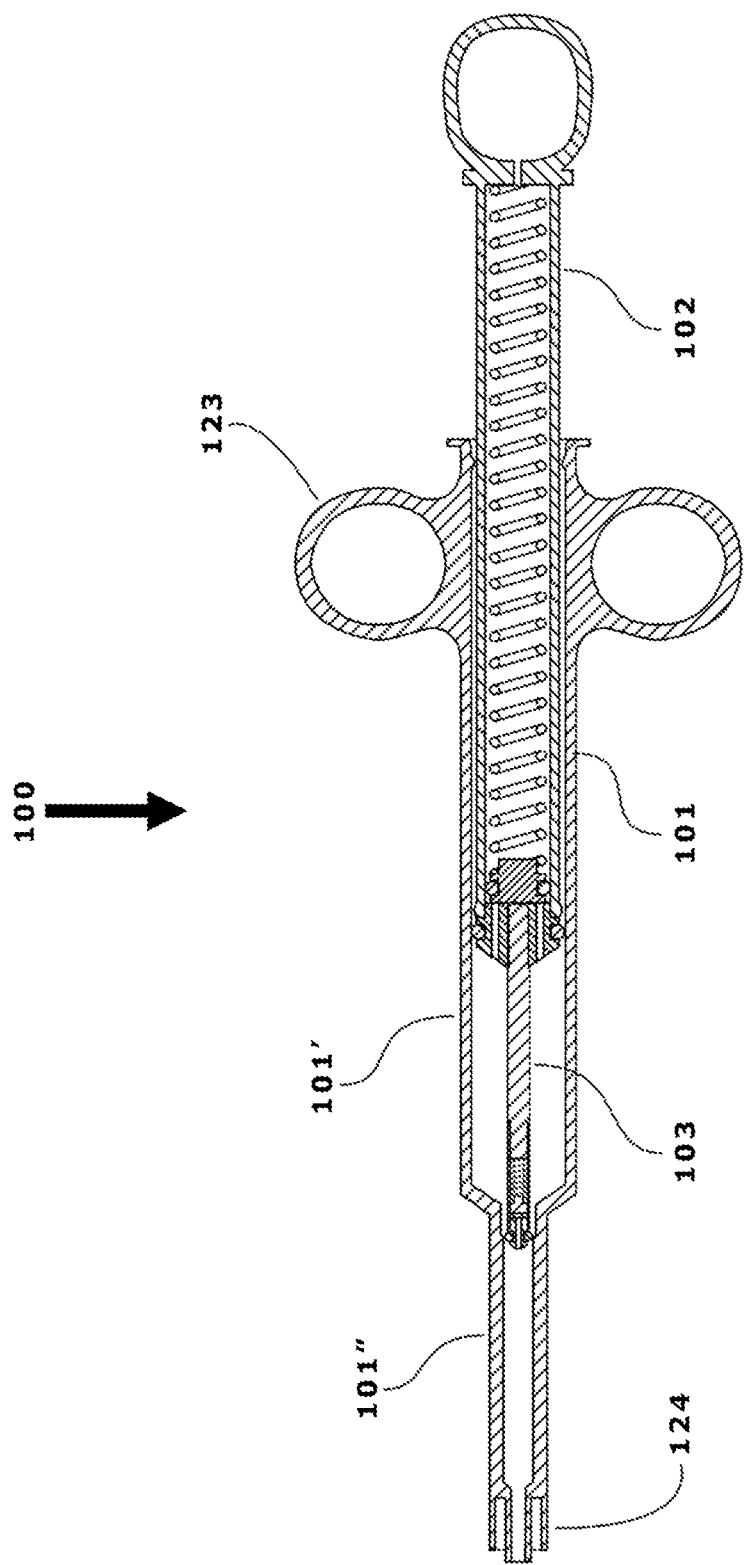

APPARATUS AND METHODS FOR INFLATING AND DEFLATING BALLOON CATHETERS

CROSS-REFERENCE TO RELATED APPLICATIONS

Pursuant to 35 U.S.C. §119(e), this application claims priority to U.S. Provisional Application No. 61/430,082 filed on Jan. 5, 2011, the disclosures of which is herein incorporated by reference in its entirety.

FIELD OF THE INVENTION

This invention generally relates to medical procedures within the human or mammalian body that utilize an inflation and/or deflation device to inflate or deflate a balloon or an inflatable membrane in procedures such as angioplasty, vertebroplasty and sinuplasty.

BACKGROUND

The use of the various devices in medical procedures entail a fair degree of manual dexterity on the part of the physician performing the procedures and frequently require the aid of one or more assistants to successfully complete the procedures. One such procedure is the inflation and deflation of balloon systems such as those employed in angioplasty, vertebroplasty, and sinuplasty with standard inflation devices. Device preparation which involves purging or evacuation of air from the balloon systems can be particularly demanding, commonly requiring the use of both hands of a single operator. Many of the medical procedures performed using balloon systems require the physician to use both hands in order to maneuver, position and hold these medical devices during the inflation or deflation steps, thus presenting the need for a second operator to accomplish procedure.

A number of commercial products are available that attempt to address one or more of the challenges associated with controlling the inflation and deflation of a balloon system. Many of these products are focused on providing precise control over the amount of pressure that is applied to the expandable member of the balloon system, as a large contingent of dilatation procedures require a relatively high amount of pressure in order to properly displace tissue, plaque, bone and the like. For example, many commercial available inflation devices comprise a syringe with a pressure gauge attached, wherein the syringe plunger is free to move longitudinally within the inner bore of the syringe barrel by pulling on a handle provided on the syringe plunger proximal end. The action of retracting the syringe plunger proximally provides a vacuum within the syringe to draw fluid or air into the syringe barrel. Conversely, pushing on the handle of the syringe plunger discharges the fluid or air out of the syringe. In a closed system (e.g. when the inflation device is attached to a balloon catheter) a sealing member (typically attached to the distal end of the syringe plunger) acts as a gasket to prevent fluid or air to leak around the gap between the inner wall of the syringe barrel and the outer surface of the syringe plunger when the syringe plunger is advanced towards the distal end of the inflation device (in order to generate pressure) or retracted proximally (in order to generate vacuum). The sealing member attached at the distal end of the syringe plunger allows the fluid or air within the closed system (the inflation/deflation device and the coupled medical device such as balloon catheter) to be compressed, increasing the internal pressure as the plunger continues to advance distally. The operator can observe the reading on the pressure gauge to ascertain that magnitude of pressure within the system. Another mechanism of inflation comprises a syringe plunger that is threaded, wherein the thread is engaged with an element of the device so that the longitudinal movement in the distal direction within the syringe barrel is effected by rotation of the threaded syringe plunger thus building up pressure within the device. The descriptions of these inflation devices are referenced in U.S. Pat. Nos. 4,743,230, 4,832,692, 5,507,727, and 7,530,970 which have been incorporated herein by reference. Other designs such as the locking syringe described in U.S. Pat. Nos. 5,047,015, 5,057,078, and 5,209,732 (herein incorporated in full by reference) allow for the selection and maintenance of a given inflation pressure.

Another method of simplifying the inflation and/or deflation of a balloon or other expandable member is illustrated in devices that allow for a pre-selected level of negative pressure to be applied and maintained without constant effort on the part of the operator. One example of this type of design is the VacLok® series of syringes available from Merit Medical. These devices comprise a polycarbonate syringe body with a stop pin and a plunger with locking fins that prevents relative motion of the plunger with respect to the syringe body when the fins are engaged with the stop pin. Vacuum is applied and maintained by retracting the syringe plunger to create a desired negative pressure, then rotating the plunger to position one of the locking fins proximal to the stop pin. The interference between the locking fin and the stop pin prevents distal motion of the plunger and the release of negative pressure. These types of designs are taught in U.S. Pat. No. 5,215,536 and are herein incorporated by reference.

Another typical inflation/deflation syringe set up that may be used for inflation and deflation of a medical device such as balloon catheter comprises a small volume syringe (e.g. 1 ml syringe), a large volume syringe (e.g. 10 ml syringe) and a manifold (e.g. 3 way manifold or stopcock) assembled together. The small volume syringe is used to provide high inflation pressures with minimal effort (due to the relatively small syringe plunger cross section), the large volume syringe is used to apply vacuum for deflation as well as serve as a reservoir for the inflation fluid media, and the manifold or stopcock functions to open or close ports enabling communication between the balloon catheter and the desired syringe. The use of the large syringe is needed as the small syringe is not capable of producing the magnitude of vacuum required for timely to deflation of the balloon, nor does it hold a sufficient volume of fluid to compensate for the void volume of the balloon catheter, inflate the balloon to a neutral pressure, and further increase the pressure in the balloon to the desired level. The method of inflation or deflation involves rotating the valve of the manifold or stopcock in order for the balloon catheter to communicate with the inflation syringe or the deflation syringe. For example, a high pressure balloon may be inflated by rotating the valve of the manifold or stopcock to open a flow path between the larger syringe and the balloon catheter. After evacuating the air in the balloon catheter, the larger syringe in depressed to fill the void volume of the balloon catheter and begin inflating the balloon. At this point, the force required to further inflate the balloon exceeds the amount that can be comfortably applied by the operator. The valve of the manifold or stopcock is rotated further to close the flow path between the larger syringe and the balloon catheter and open a flow path between the smaller syringe and the balloon catheter. The operator continues to inflate the balloon to the desired pressure by depressing the smaller syringe. Once the desired pressure has been achieved, the valve of the manifold or stopcock is rotated to close all flow paths between the syringes and the balloon catheter. Deflation of the balloon is achieved by rotating the valve of the manifold or stopcock to open a flow path between the larger syringe and the balloon catheter and retracting the plunger of the larger syringe to generate a negative pressure in the syringe barrel. The negative pressure draws fluid out of the balloon catheter and deflates the balloon. In this set up, it is apparent that there is an added operator burden or difficulty since the operation involves several manipulations of a stopcock or manifold in order for the system to operate correctly.

While these inflation devices have utility, they are not the most efficient and convenient for the physician and medical staff to use in the field due to the need for two hands to successfully operate the devices, the ergonomics and bulk of the current designs, and the number steps needed to prepare and deploy the inflation mechanism.

An inflation and/or deflation device that would simplify the dilation of an expandable member, such as a balloon catheter, that can be successfully operated with one hand would relieve the burden placed on the physician operator and associated staff during often complex medical procedures, and thus potentially presents a labor cost savings.

RELEVANT LITERATURE

U.S. Pat. Nos. 4,743,230; 4,832,692; 5,047,015; 5,057,078; 5,209,732; 5,215,536; 5,507,727; and 7,530,970.

SUMMARY OF THE INVENTION

This invention is directed to improve the inflation/deflation of balloon dilation systems as used in angioplasty, vertebroplasty, sinuplasty, and similar procedures by allowing a user to achieve a high inflation pressure with a single hand.

This invention relates to a device that has the ability to inflate a balloon or other inflatable structures.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 1A-1C depict cross-sectional views of an embodiment of the invention comprising a pressure limiting feature and a series deflation and inflation syringe arrangement.

DETAILED DESCRIPTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the polymer" includes reference to one or more polymer and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1B:
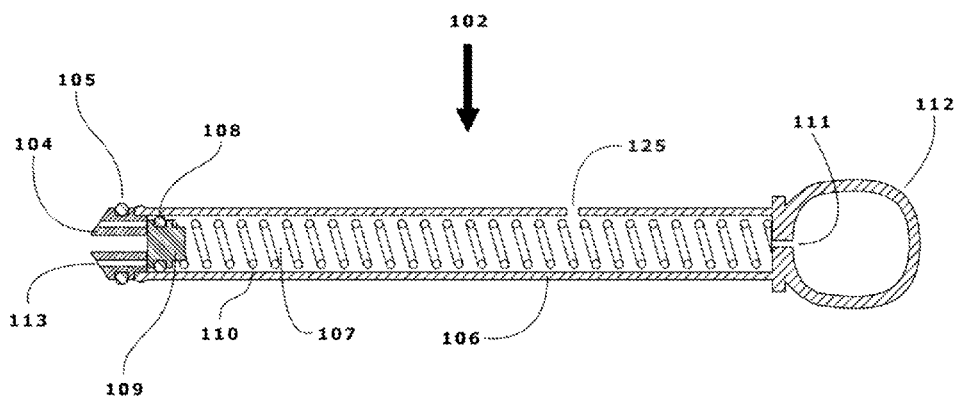
Figure 1C:
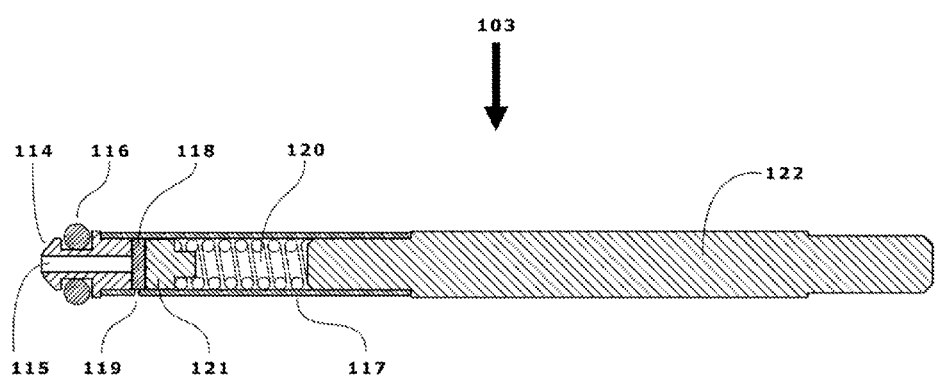

FIGS. 1A-1C illustrate one embodiment of the invention. Inflation/deflation syringe 100 is comprised of a syringe barrel 101, a deflation plunger 102, and an inflation plunger 103. The syringe barrel 101 is comprised of at least two integrated syringe barrel chambers, 101' and 101", with at least two different cross sectional inner diameters, preferably oriented in a serial configuration. The syringe barrel 101 configuration in the preferred embodiment comprises a smaller volume syringe barrel chamber 101" (e.g. with a volume capacity of about 1 ml), located in series and preferably distal to the larger volume syringe barrel chamber 101' (e.g. with a volume capacity equal to or greater than 5 ml). The smaller volume syringe barrel chamber 101" is dimensioned to have a relatively small inner diameter and is used as the inflation chamber. The larger volume syringe barrel chamber 101' is dimensioned to have a larger inner diameter relative the smaller volume syringe barrel and is used as the deflation chamber as well as a reservoir for inflation fluid media such as air or liquid. Disposed within the syringe barrel 101 are deflation plunger 102 and inflation plunger 103, oriented in series, each plunger sized to fit inside one of the individual inner diameters of the syringe barrel 101. The smaller diameter inflation plunger 103 fits inside the smaller syringe barrel chamber 101" and the larger diameter deflation plunger 102 fits inside the larger syringe barrel chamber 101'. The distal most tip of syringe barrel 101 comprises a port connector 124 that enables fluid and/or air communication between inflation/deflation syringe 100 and an external device. Port connector 124 may include but is not limited to fixed male or female luer lock fittings, rotating male or female luer lock fittings, hose barbs, slip luers, quick release fittings, and the like. In place of a port connector provided at the distal end of the syringe barrel 101, an extension line or tubing (not shown) may be permanently attached to the distal end of the syringe barrel 101 and the port connector 124 may attached to the distal end of the extension line (not shown). Syringe barrel 101 also comprises at least one ring 123 or a similar feature, including but not limited to flanges, indentations, wings, bars, grips, and the like, that may be used by the operator to allow the syringe body to be single-handedly held and to provide stability when advancing or retracting the deflation plunger 102. Syringe barrel 101 may be fabricated from materials known in the art, including but not limited to polycarbonate, polypropylene, polymethylmethacrylate, PET, PEEK, stainless steel, brass, aluminum, titanium, borosilicate glass, ceramics, and the like or combinations thereof, and may be transparent, translucent, opaque, or any gradient thereof.

As shown in FIG. 1B, deflation plunger 102 further comprises a deflation plunger tip 104, deflation plunger tip port 113, deflation plunger seal 105, deflation plunger body 106, deflation plunger chamber 107, piston seal 108, piston 109, piston return spring 110, pressure release port 111, media release port 125, and plunger ring 112. Deflation plunger body 106 may be fabricated from materials known in the art, including but not limited to polycarbonate, polypropylene, polymethylmethacrylate, PET, PEEK, stainless steel, brass, aluminum, titanium, borosilicate glass, ceramics, and the like or combinations thereof, and may be transparent, translucent, opaque, or any gradient thereof. Deflation plunger tip 104 is joined the distal end of deflation plunger 106 using methods known in the art, including but not limited to press fitting, adhesive bonding, ultrasonic welding, threading/tapping, heat fusing, overmolding, use of a set screw, and the like and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium and the like or combinations thereof. The deflation plunger tip 104 and the deflation plunger body 106 may be integrated and manufactured as single component by means of commonly known fabrication techniques such as machining, injection molding, casting, and the like. The deflation plunger tip 104 may comprise at least one deflation plunger tip port 113. Deflation plunger tip port 113 may be fabricated using methods known in the art including, but not limited to laser cutting and or engraving, mechanical machining, electrical discharge machining, chemical etching, and the like. Alternatively, deflation plunger tip port 113 may be formed in deflation plunger tip 104 as a feature of deflation plunger tip 104 during a molding process. Deflation plunger seal 105 is sized and arranged such that it provides an air and/or fluid tight seal between the deflation plunger tip 104 and the inner surface of larger syringe barrel 101' and may be fabricated from materials including, but not limited to polychloroprene, silicone rubber, nitrile rubber, Viton®, EPDM, butyl rubber, natural rubber, polyethylene, and the like. While deflation plunger seal 105 is depicted as an o-ring in FIG. 1B, it should be clear to those of skill in the art that equivalent components such as gaskets may be interchanged with deflation plunger seal 105. For example, deflation plunger seal 105 may be an integral part of deflation plunger tip 104, such as one or more flanges molded, machined, or otherwise manufactured as a feature of deflation plunger tip 104 that provides an air and/or liquid tight seal between deflation plunger tip 104 and the inner surface of larger syringe barrel 101'. Piston 109 coaxially resides within deflation plunger chamber 107 and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Piston 109 is biased by piston return spring 110 such that the distal face of piston 109 is positioned against the proximal face of deflation plunger tip 104. Piston seal 108 may be held within a feature such as a groove or channel on piston 109, and is sized such that it creates an air and/or liquid tight seal between piston 109 and the inner surface of deflation plunger body 106 while allowing translation of piston 109 along deflation plunger chamber body 106 and may be fabricated from materials including, but not limited to polychloroprene, silicone rubber, nitrile rubber, Viton®, EPDM, butyl rubber, natural rubber, polyethylene, and the like. While piston seal 108 is depicted as an o-ring in FIG. 1B, it should be clear to those of skill in the art that equivalent components such as gaskets may be interchanged with piston seal 108. For example, piston seal 108 may be an integral part of piston 109, such as one or more flanges molded, machined, or otherwise manufactured as a feature of piston 109 that provides an air and/or liquid tight seal between piston 109 and the inner surface of deflation plunger body 106. Piston return spring 110 resides within deflation plunger chamber 107, and has a combination of spring rate, length, pitch, wire thickness, and outer diameter such that the distal end of piston return spring 110 places a compressive load against the piston 109. Piston return spring 110 may be fabricated from materials known in the art including but not limited to high carbon wire, alloy steel, stainless steel, nitinol, non-ferrous alloy, high-temperature alloy, and the like. Pressure release port 111 is provided to prevent pressure build up inside the deflation plunger chamber when the piston moves proximally. Plunger ring 112 may be comprised of at least one ring or a similar feature, including but not limited to flanges, indentations, wings, bars, grips, and the like, that may be used by the operator to allow the deflation plunger 102 to be held with a single hand and provide stability when advancing or retracting the deflation plunger 102. Media release port 125, located at the proximal side of the deflation plunger body 106, may be incorporated as an overflow port for the excess air or fluid contained inside the syringe barrel 101. Preferably, the pressure release port is located distal of the piston seal 108 when the piston return spring 110 is fully compressed.

FIG. 1C shows inflation plunger 103 in detail, comprising inflation plunger tip 114, inflation plunger tip port 115, inflation plunger seal 116, inflation plunger housing 117, face seal 118, outlet port 119, pressure control spring 120, pressure control piston 121, and inflation rod 122. The proximal end of inflation rod 122 is attached to the deflation plunger tip 104; the two components may be joined by methods known in the art including but not limited to press fitting, adhesive bonding, ultrasonic welding, threading/tapping, overmolding, heat fusing use of a set screw, and the like. Alternatively, inflation rod 122 and deflation plunger tip 104 may be machined, molded, cast or otherwise formed as a single component. Yet another alternative configuration is to fabricate the inflation rod 122, deflation plunger tip 104 and deflation plunger body 106 as a single component by means of machining, molding, casting or the like. Inflation rod 122 may be fabricated from materials known in the art including but not limited to polycarbonate, polypropylene, polymethylmethacrylate, polyurethane, nylon, Pebax, PET, PEEK, Delrin®, PTFE, stainless steel, brass, aluminum, titanium and the like or combinations thereof. The proximal end of inflation plunger housing 117 is joined to the distal end of inflation rod 122 by methods known in the art that include but are not limited to press fitting, adhesive bonding, ultrasonic welding, threading/tapping, overmolding, use of a set screw, and the like and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Alternatively, inflation plunger housing 117 and inflation rod 122 may be machined, molded, or otherwise formed as a single integrated component. Inflation plunger housing 117 further comprises outlet port 119. Outlet port 119 may be fabricated using methods known in the art including but not limited to laser cutting and or engraving, mechanical machining, electrical discharge machining, chemical etching, and the like. Alternatively, outlet port 119 may be formed in inflation plunger housing 117 as a feature of inflation plunger housing 117 during a molding process. Inflation plunger tip 114 is joined to the distal end of inflation plunger housing 117 using methods known in the art including, but not limited to press fitting, adhesive bonding, ultrasonic welding, threading/tapping, overmolding, heat fusing, use of a set screw, and the like and may be fabricated from materials known in the art including, but not limited to polycarbonate, polypropylene, polymethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Inflation plunger tip 114 further comprises at least one inflation plunger tip port 115 extending from the distal to proximal ends of inflation plunger tip 114, and may be fabricated using methods known in the art including, but not limited to laser cutting and or engraving, mechanical machining, electrical discharge machining, chemical etching, and the like. Alternatively, inflation plunger tip port 115 may be formed in inflation plunger tip 114 as a feature of inflation plunger tip 114 during a molding process. Inflation plunger seal 116 may be held within a feature such as a groove or channel on inflation plunger tip 114, and is sized such that it creates an air and/or liquid tight seal between inflation plunger tip 114 and the inner surface of smaller syringe barrel 101" and may be fabricated from materials including, but not limited to polychloroprene, silicone rubber, nitrile rubber, Viton®, EPDM, butyl rubber, natural rubber, polyethylene, and the like. While inflation plunger seal 116 is depicted as an o-ring in FIG. 1C, it should be clear to those of skill in the art that equivalent components such as gaskets may be interchanged with inflation plunger seal 116. For example, inflation plunger seal 116 may be an integral part of inflation plunger tip 114, such as one or more flanges molded, machined, or otherwise manufactured as a feature of inflation plunger tip 114 that provides an air and/or liquid tight seal between inflation plunger tip 114 and the inner surface of smaller syringe barrel 101". Face seal 118 resides inside inflation plunger housing 117 and is sized to provide an air and/or fluid tight seal when pressed against the proximal end of the inflation plunger tip 114. Face seal 118 may be fabricated from materials known in the art including but not limited to polychloroprene, silicone rubber, nitrile rubber, Viton®, EPDM, butyl rubber, natural rubber and the like. The distal face of pressure control piston 121 contacts the proximal surface of face seal 118. Pressure control piston 121 may be joined to face seal 118 or the two components may be decoupled from each other. Methods of joining the two components may comprise but are not limited to press fitting, adhesive bonding, ultrasonic welding, threading/tapping, overmolding, use of a set screw, and the like. Pressure control piston 121 may be fabricated from materials including but not limited to polycarbonate, polypropylene, polymethylmethacrylate, polyurethane, nylon, Pebax, PET, PEEK, Delrin®, PTFE, stainless steel, brass, aluminum, titanium and the like or combinations thereof. Alternatively, the pressure control piston 121 and the face seal 118 may be combined and may be made of a single component. Yet another alternative configuration is to eliminate the use of pressure control piston 121 by incorporating the features of the piston 121 to the face seal 119. The proximal end of pressure control piston 121 serves as a base to stabilize the distal end of pressure control spring 120. Pressure control spring 120 resides within inflation plunger housing 117 such that the distal end of pressure control spring 120 places a compressive load on pressure control piston 121. Pressure control piston 121 transmits at least some of the compressive load applied by pressure control spring 120 to the proximal surface of face seal 118, thus maintaining a seal between inflation plunger tip 114 and the distal surface of face seal 118. Pressure control spring 120 maintains this seal until a desired pressure is exceeded; this pressure is dictated by the force (or spring force constant) of pressure control spring 120 at a given length of compression by specifying the overall length, pitch, wire thickness, wire material and outer diameter of pressure control spring 120. Pressure control spring 120 may be fabricated from materials known in the art including but not limited to high carbon wire, alloy steel, stainless steel, nitinol, non-ferrous alloy, high-temperature alloy, and the like.

Alternatively (not shown), deflation plunger seal 105 and inflation plunger seal 116 may reside on a channel, groove, or similar feature of larger syringe barrel 101' and smaller syringe barrel 101", respectively, that allow for hermetic seals between larger syringe barrel 101' and deflation plunger 102, and smaller syringe barrel 101" and inflation plunger 103. In this embodiment, the outlet port 119 is positioned or located proximal of the inflation plunger seal 116 when the deflation plunger 102 is fully depressed into syringe barrel 101. The outlet port 119 may be incorporated to the inflation rod 122 by way of providing an inner lumen or opening (not shown) through the length of inflation rod 122 originating from the distal end and terminating at the proximal end of the inflation rod 122. Alternatively, the location of inflation plunger housing 117, face seal 118, pressure control spring 120, and pressure control piston 121, may be positioned proximally (not shown) by increasing the length of the inflation plunger tip 114 and decreasing the length of the inflation rod 122, thus shifting the outlet port 119 proximal of the inflation plunger seal 116 when the deflation plunger 102 is fully depressed into syringe barrel 101.

Figure 2A:
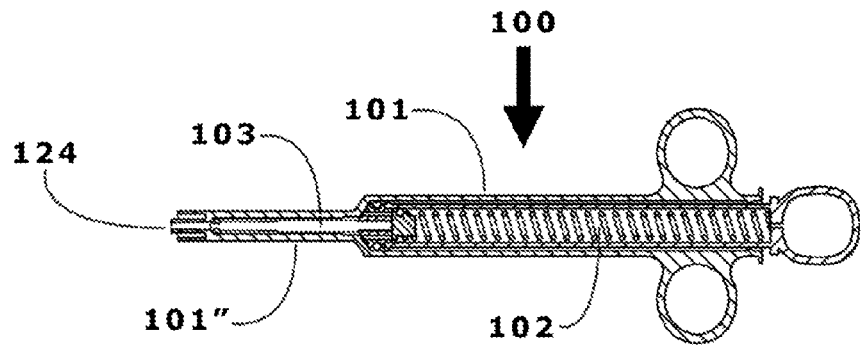
FIGS. 2A-2E depict a method of operation of the embodiment of the invention illustrated in FIGS. 1A-1C.
Figure 2B:
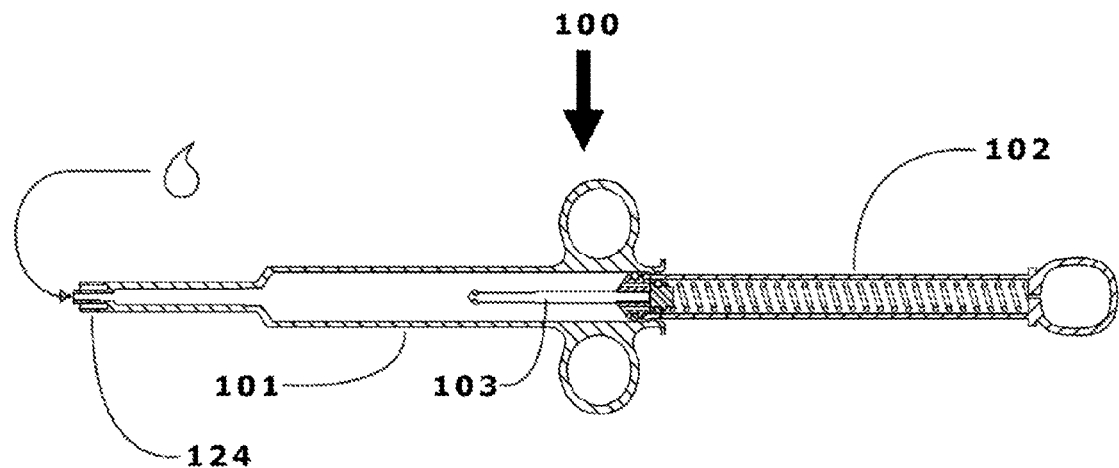
Figure 2C:
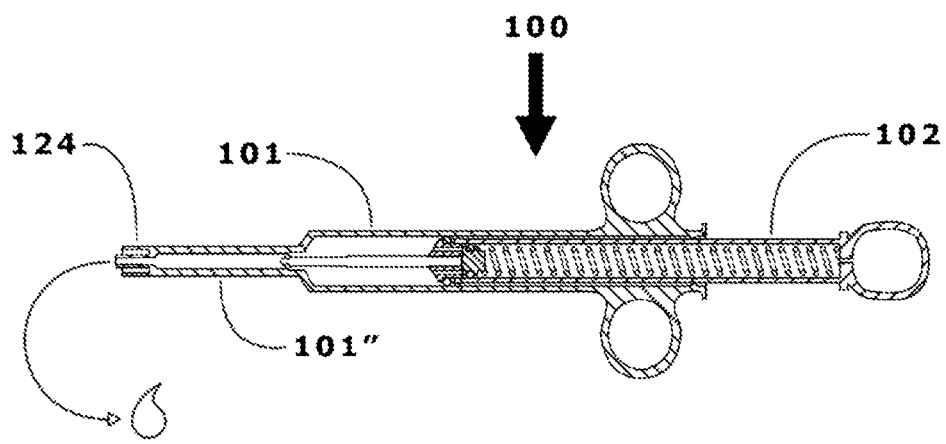

FIGS. 2A-2E illustrate a method of the using one embodiment of the inflation/deflation syringe of the invention. The inflation/deflation syringe 100 can be used to inflate and deflate an inflatable element (not shown) of a medical device such as balloon catheter (not shown) and the like. FIG. 1A shows the relative position of the elements of the components of the invention in an initial configuration wherein the deflation plunger 102 is advanced until the inflation plunger tip is at the distal side of the smaller syringe barrel 101". The syringe barrel 101 is then filled with inflation media, preferably a fluid, by fully retracting the deflation plunger 102 to the position shown in FIG. 2B. This step can be repeated until the syringe barrel 101 is sufficiently filled with inflation media such that when the inflation/deflation syringe 100 is held vertically with the distal end pointing up, the level of the inflation media is above the distal tip of the inflation plunger 103. Excess inflation media and/or air or air bubbles above the fluid level inside the syringe barrel 101 the can be purged out by advancing the deflation plunger 102, while the syringe 100 is held vertically, and further advanced until the distal tip of the inflation plunger 103 is aligned at or near the proximal end of the smaller syringe barrel 101" as shown in FIG. 2C. A visual indicator (not shown) such as printed markers or the like, or a tactile indicator such as detents or the like, may be incorporated into the inflation/deflation syringe 100 to aid the user in filling the lumen of the syringe barrel 101 with the proper amount or volume of inflation media. The syringe port connector 124 may then be attached to the medical device inflation port. Alternatively, an inflation line extension (not shown) may be attached to the syringe port connector 124 prior to purging the excess inflation media. Once the inflation line extension is connected, excess inflation media and/or air or air bubbles above the fluid level inside the syringe barrel 101 the can be purged out by advancing the deflation plunger 102 while the syringe 100 is held vertically. At this point, the inflation line lumen (not shown) should be filled with inflation media and the distal end of the extension line can be attached to a medical device such as a balloon catheter, for example.

Figure 2D:
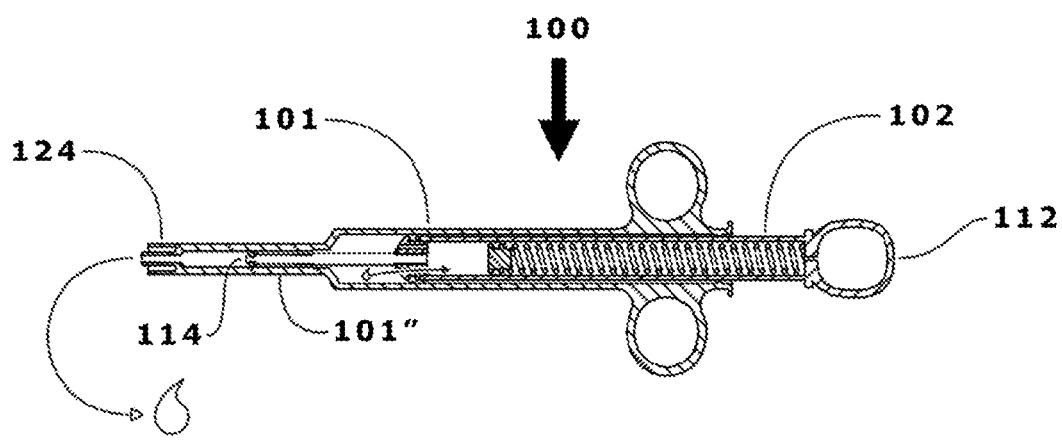
Figure 2E:
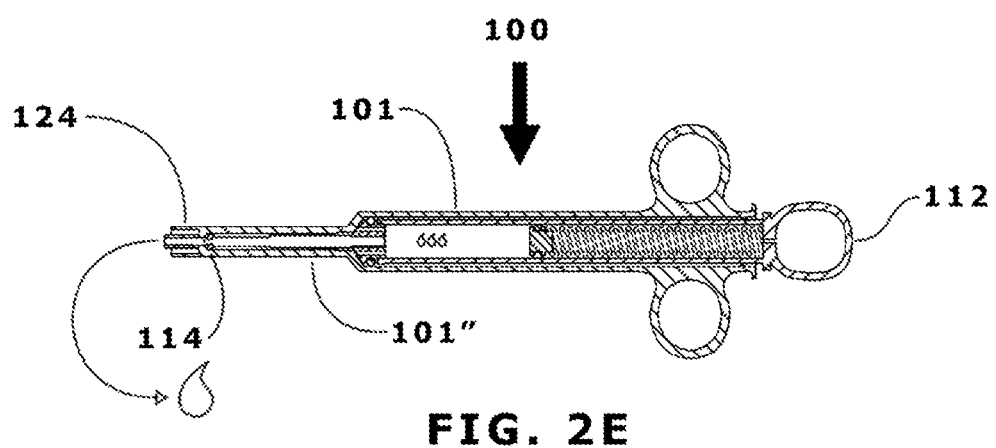

The balloon catheter may be prepared by aspirating the air out of the balloon inflation path by fully retracting the deflation plunger 102 and allow the air/air bubbles to be purged out (not shown). This is done by holding the syringe 100 such that the distal tip is pointed down prior to retracting the deflation plunger 102 and then releasing to neutral. FIGS. 2D and 2E show the subsequent one-handed inflation of the balloon catheter. The user may press on the deflation plunger ring 112 until the inflation plunger tip 114 is at the end of the advancement stroke. The balloon may then be deflated by fully retracting the deflation plunger 102. Once the balloon of the medical device is deflated, the deflation plunger 102 can be released and place back to neutral position.

Figure 3A:
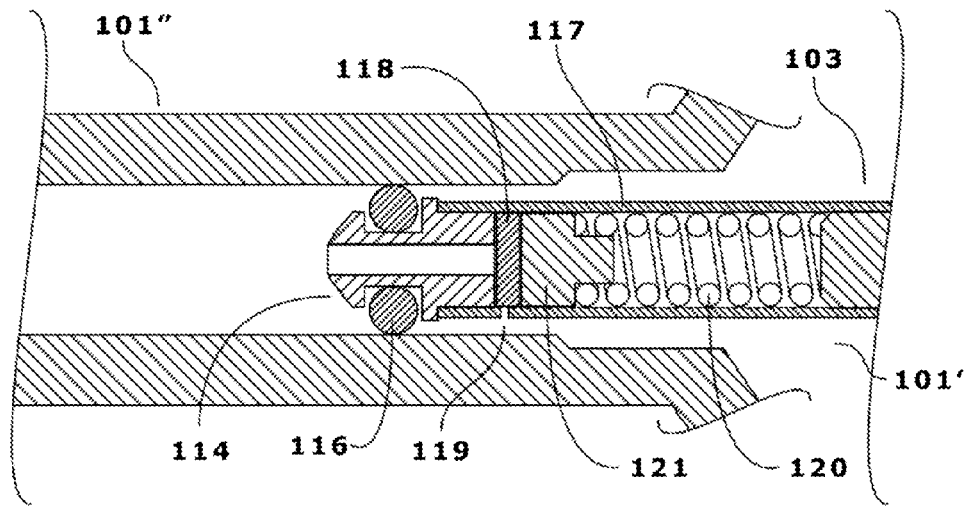
FIGS. 3A-3B depict a magnified view of the operation of the pressure control mechanism.
Figure 3B:
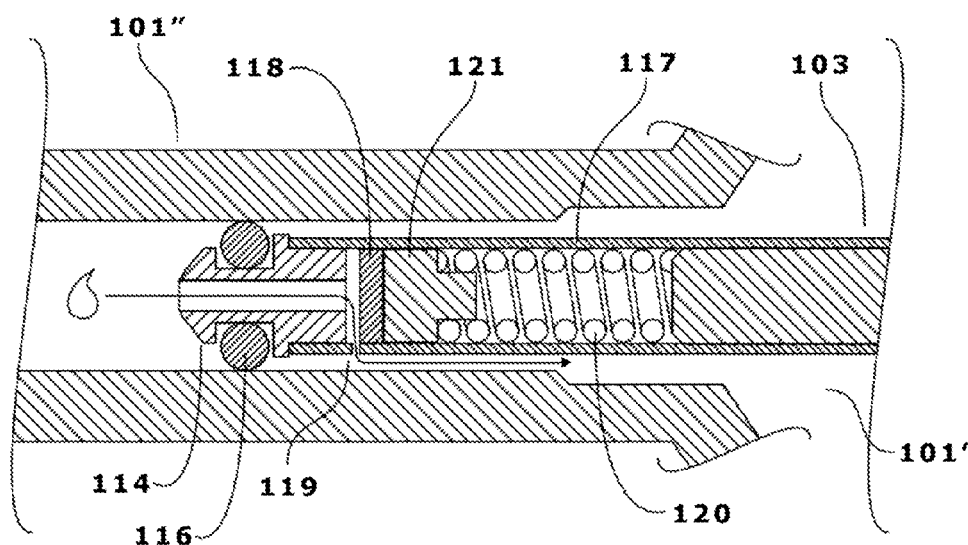

FIGS. 3A and 3B detail one unique aspect of the preferred embodiment; the pressure control mechanism incorporated in the design of the inflation plunger 103 which limits the maximum pressure being applied to the medical device. The maximum internal pressure generated inside the distal portion of smaller syringe barrel 101" during the advancement of the inflation plunger 103 is limited or regulated by the pressure control mechanism contained inside the inflation plunger housing 117. The pressure control mechanism is comprised of the face seal 118, pressure control piston 121 and pressure control spring 120. The maximum inflation pressure is determined or regulated by the degree or amount of compression force applied by the pressure control spring 120 to the pressure control piston 121 that presses the face seal 118 against the proximal face of the inflation plunger tip 114. FIG. 3A shows the pressure control mechanism in a closed state, wherein the pressure in the smaller syringe barrel 101" distal to the inflation plunger seal 116 is below that of a pre-determined value. Under these conditions, outlet port 119 is closed and there is no fluid and/or air flow path between the distal portion of smaller syringe barrel 101" and larger syringe barrel 101'. FIG. 3B illustrates the pressure control mechanism in the open state, wherein the internal pressure inside the distal portion of the smaller syringe barrel 101" exceeds a pre-determined value. In this state, the internal pressure inside the distal portion of smaller syringe barrel 101" exceeds that of the pre-determined pressure exerted by the face seal 118 against the inflation plunger tip, compressing the pressure control spring 120 and moving face seal 118 proximally. The movement of face seal 188 opens a flow path at the contact interface between face seal 118 and inflation plunger tip 114. Further movement of the face seal 118 to a position proximal to outlet port 119 creates a flow path between the distal portion of smaller syringe barrel 101" and larger syringe barrel 101'. The excess pressure inside the distal portion of smaller syringe barrel 101" is reduced as the inflation media flows through the outlet port 119, along the proximal portion of smaller syringe barrel 101", and into larger syringe barrel 101'. When the internal pressure inside the distal portion of smaller syringe barrel 101" falls below the pre-determined level, compression spring 120 expands and applies force to pressure control piston 121, which in turn moves distally and re-establishes the interface between face seal 118 and the proximal face of inflation plunger tip 114. The value of the pre-determined pressure may be adjusted by changing the force constant of the compression spring 120, the resting length of the compression spring 120, the distance between outlet port 119 and the proximal edge of inflation plunger tip 114, the static or dynamic friction between the face seal and the internal surface of the inflation plunger housing 117, the static or dynamic friction between the pressure control piston 121 and the inflation plunger housing 117, or the durometer of face seal 118 and/or pressure control piston 121 among other methods known in the art. While the pressure control mechanism has been depicted as a spring and seal combination in this embodiment, other valve and/or seal mechanisms including but not limited to ball valves, duckbill valves, umbrella valves, check valves, diaphragms, shuttling valves, flap valves and the like may be incorporated into the mechanism.

Figure 4A:
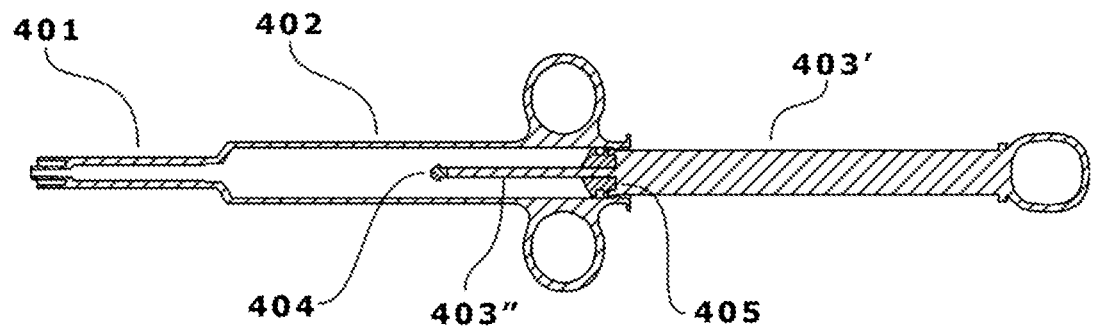
FIGS. 4A-4B depict a serial syringe arrangement without incorporating the additional features of the present invention.
Figure 4B:
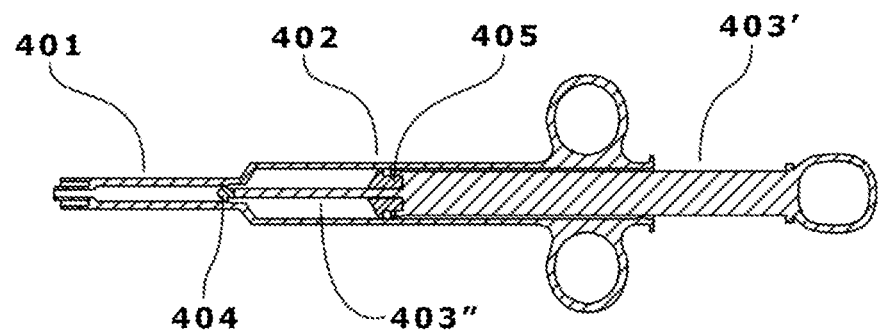

Another unique aspect of the inflation/deflation syringe 100 of the invention is the capacity to both inflate and deflate the balloon of a medical device by advancing or retracting the coupled deflation plunger 102 and inflation plunger 103 simultaneously inside a combined or integrated syringe barrel 101 that comprises two different diameters and/or volumes. FIG. 4A illustrates a typical tandem syringe set up two sizes of syringe body are connected and arranged in series with the smaller syringe body 401 positioned distal to the larger syringe body 402. The syringe plunger 403 in such a system is sized to reside within the tandem syringe; this may be accomplished through the use of a stepped design that has a smaller distal section 403" that matches the smaller syringe body 401 and a larger proximal section 403' that matches the proximal syringe body 402 such that the syringe plunger 403 can translate along the length of the syringe body. In these types of systems, it is often not possible to generate a sufficiently high internal pressure inside the smaller syringe body 401 (and in any medical equipment connected to the smaller syringe body). Once the distal plunger seal 404 engages and seals against the inside wall of the smaller syringe body chamber 401 (as shown in FIG. 4B), the inflation fluid is trapped within the larger syringe body chamber. The incompressible inflation fluid trapped between distal plunger seal 404 and proximal plunger seal 405 then prevents the syringe plunger 403 from advancing further and increasing the pressure inside the smaller syringe body 401.

Figure 5A:
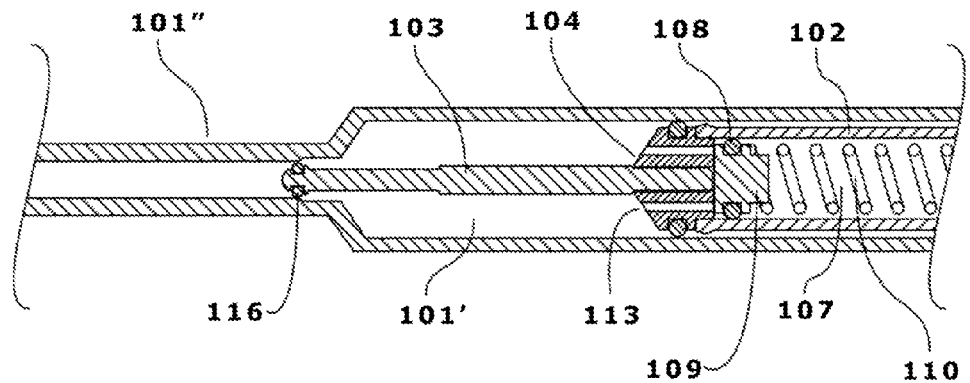
FIGS. 5A-5B depict a magnified view of the deflation plunger during the inflation process.
Figure 5B:
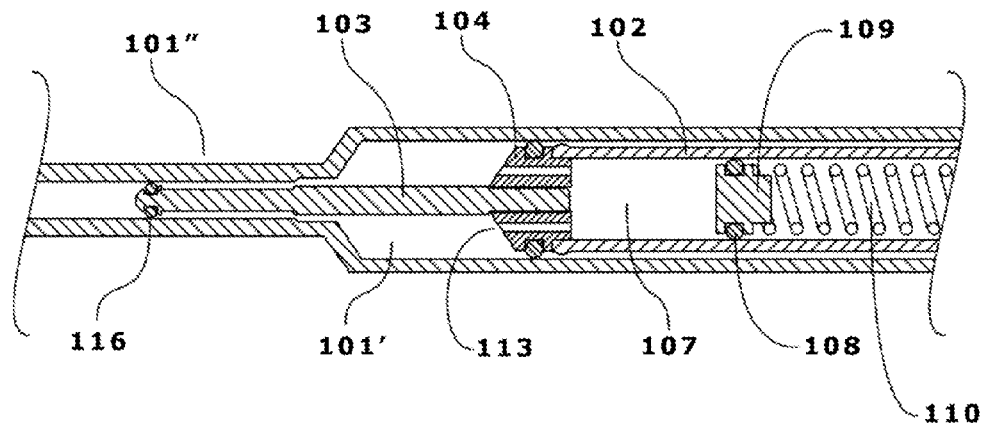

The unique design of the present invention illustrated in FIGS. 5A and 5B allows the plungers 102 and 103 to be advanced further by incorporating a deflation plunger tip port 113 that allows the incompressible fluid trapped inside the larger syringe barrel 101' to be displaced and transferred to the deflation plunger chamber 107. FIG. 5A depicts the arrangement of the components of the invention at the point when the inflation plunger seal 116 initially contacts and seals against the inner wall of the smaller syringe barrel 101". The distal face of the piston 109 is in contact with the proximal face of the deflation plunger tip 104, closing the potential flow path through the deflation plunger tip port 113. FIG. 5B depicts the arrangement of the components of the invention after the syringe plungers 102 and 103 are further advanced distally. As syringe plungers 102 and 103 translate distally, the piston 109 and piston seal 108 assembly is pushed back proximally and the incompressible inflation fluid is directed through deflation plunger tip port 113 and transferred inside the deflation plunger chamber 107. The piston 109 and piston seal 108 assembly provides a leak free seal that keeps the inflation fluid inside the deflation plunger chamber 107. When the plungers 102 and 103 are retracted for deflation (not shown), the incompressible inflation fluid inside the deflation plunger chamber 107 is returned to smaller syringe barrel 101' through deflation plunger tip port 113. The retraction of syringe plungers 102 and 103 creates a negative pressure inside the larger syringe barrel 101'. The negative pressure (with respect to the ambient pressure on the proximal side of the piston 109 and piston seal assembly 108) draws the inflation fluid into larger syringe barrel 101' and pulls the piston 109 and piston seal 108 assembly distally within the deflation plunger chamber 107. The piston return spring 110 maintains the piston 109 in a normally biased position against the proximal face of deflation plunger tip 104 when the pressure in larger syringe barrel 101' is less than that applied by the piston return spring 110 to the piston 109.

Figure 6:
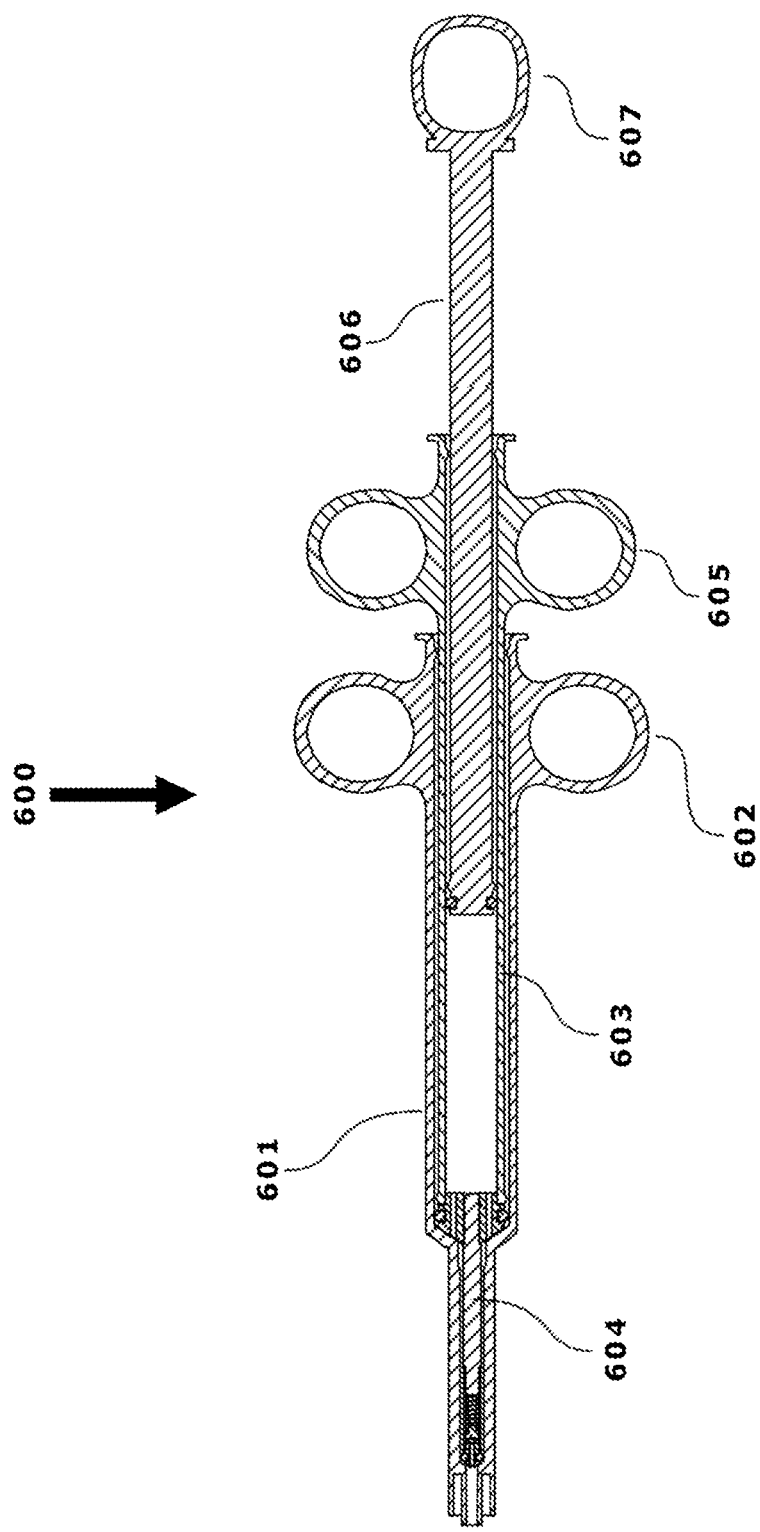
FIG. 6 depicts a cross section of an embodiment of the invention comprising a movable plunger.

Yet another alternative configuration of the present invention is shown in FIG. 6. Inflation/deflation syringe 600 comprises a syringe body 601, a deflation plunger 603, an inflation plunger 604, and movable plunger 606. As described earlier for syringe body 601, the syringe body 601 is comprised of at least two integrated syringe barrels with at least two different cross sectional inner diameters, preferably oriented in series or tandem configuration. The syringe body 601 configuration in the preferred embodiment comprises of a smaller volume syringe body (e.g. with a volume capacity of about 1 ml), located in series and preferably distal of the larger volume syringe body (e.g. with a volume capacity equal to or greater than 5 ml). The smaller volume syringe body is dimensioned to have a relatively small inner diameter and is used as the inflation chamber whereby the larger volume syringe body is dimensioned to have a larger inner diameter relative the smaller volume syringe barrel and is used as the deflation chamber as well as a reservoir for inflation fluid media such as air or liquid. Syringe body 601 also comprises at least one ring 602 or a similar feature, including but not limited to flanges, indentations, wings, bars, grips, and the like, that may be used by the operator to allow the syringe body to be single-handedly held. Deflation plunger 603 further comprises a deflation plunger tip, deflation plunger tip port, deflation plunger seal, and a deflation plunger chamber as described earlier for deflation plunger 103. Inflation plunger 604 further comprises an inflation plunger tip, an inflation plunger tip port, an inflation plunger seal, an inflation plunger housing, a face seal, an outlet port, a pressure control spring, a pressure control piston, and an inflation rod as described earlier for inflation plunger 104. Deflation plunger 603 further comprises at least one ring 605 or a similar feature, including but not limited to flanges, indentations, wings, bars, grips, and the like, that facilitate movement of deflation plunger 603 with respect to syringe body 601. Movable plunger 606 is slidably disposed within the lumen of deflation plunger 603 and comprises a gasket that provides an air and/or fluid tight seal between movable plunger 606 and the inner surface of deflation plunger 603 and at least one ring 607 or a similar feature, including but not limited to flanges, indentations, wings, bars, grips, and the like, that facilitate movement of movable plunger 606 with respect to syringe body 601 and/or deflation plunger 603. A return spring such as return spring 110 may or may not be present. If present, the return spring would reside in the lumen of deflation plunger 603 and bias the distal tip of the movable plunger against the proximal face of the deflation plunger tip component of the deflation plunger 603.

Figure 7A:
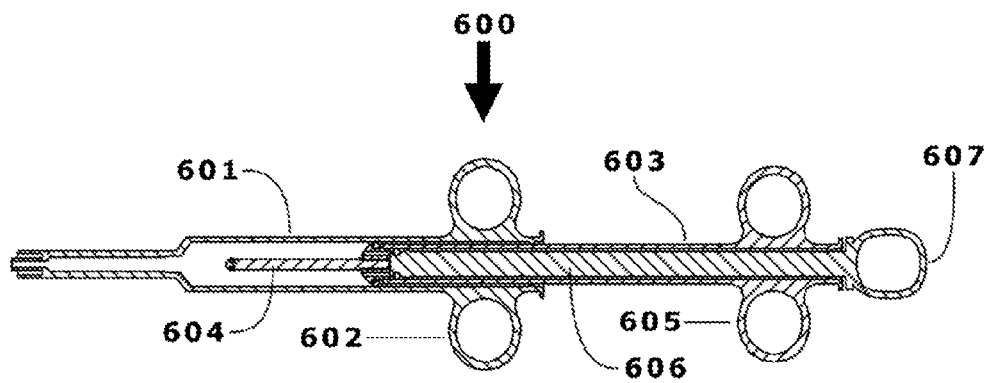
FIG. 7A-7C depict a method of operation of the embodiment of the invention illustrated in FIG. 6.
Figure 7B:
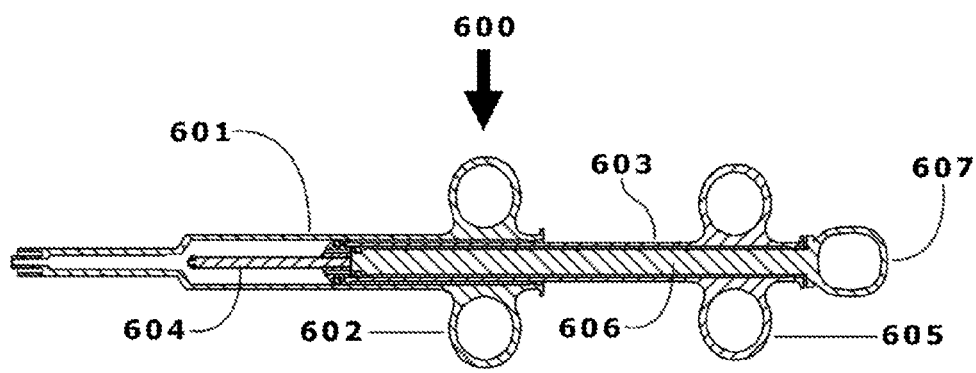
Figure 7C:
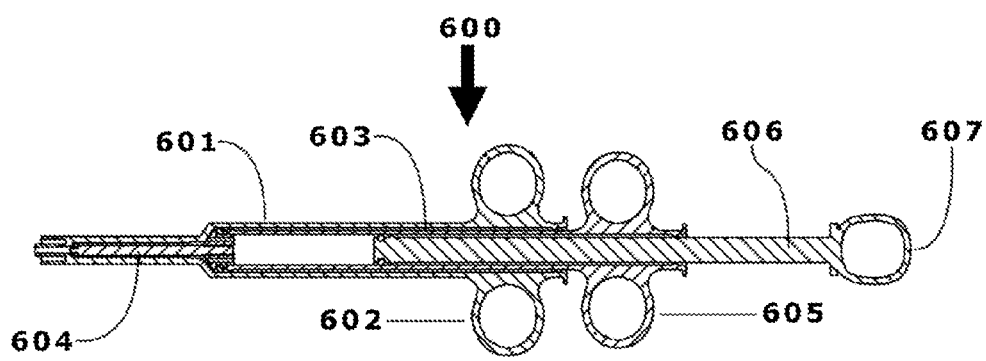

FIGS. 7A-7C illustrate a method of using this composition of the invention. FIG. 7A depicts the inflation/deflation syringe 600 in a prepped state, wherein the inflation plunger 604, deflation plunger 603, and movable plunger 606 are retracted and the lumen of the syringe body 601 is filled with the inflation media. The volume or amount of inflation fluid drawn into the lumen of the syringe body 601 will correspond to the volume needed to fill the balloon and generate high pressure within the balloon. A visual indicator (not shown) such as printed markers or the like, or a tactile indicator such as detents or the like, may be incorporated into the inflation/deflation syringe 600 to aid the user in filling the lumen of the syringe body 601 with the proper amount or volume of inflation media. The distal end of movable syringe 606 is seated against the distal wall of deflation plunger 603. FIG. 7B depicts the state of the inflation/deflation syringe 600 as movable plunger 606 begins to advance in the distal direction, introducing the inflation media into an attached medical device (not shown), such as a balloon catheter. As the void volume of the medical device is filled with inflation media and the balloon begins to expand, the pressure in the balloon increases. High pressure inflation of the balloon is achieved by fully depressing the deflation plunger 603 and inflation plunger 604 as shown in FIG. 7C. This may be done by grasping rings 602 and 605 and sliding ring 605 distally towards ring 602. Deflation of the balloon (not shown) may be accomplished by grasping rings 602 and 605 and sliding ring 605 proximally until a sufficient vacuum is generated in the lumen of syringe body 601 such that the balloon is deflated in an appropriate length of time. The utility of this type of design configuration may be particularly useful when inflating a large balloon diameter and/or long balloon length where the volume of inflation media required to fill the balloon prior to generating high pressure is more than the volume capacity of the small syringe commonly used to inflate and pressurize the balloon.

In yet another embodiment, the pressure control mechanism comprised of the face seal 118, pressure control piston 121, pressure control spring 120, along with the associated components such as inflation plunger tip port 115, inflation plunger housing 117 and outlet port 119 can be eliminated and replaced with a standard inflation plunger (not shown) and seal 116 configuration. In this configuration, the internal pressure generated inside the smaller syringe barrel 101" is not limited. However, this internal pressure can be monitored by adding a pressure gage or indicator or sensor with indicator (not shown) at the distal end of the syringe body where it is in communication with the inflation fluid path. The pressure gage or indicator set up is typically seen on standard inflation devices as described earlier. The difference between the device described in this invention and that of a typical inflation device is the ability of the user to use a single hand to generate very high pressure inflation in a controlled manner. Very high inflation pressure as defined in this embodiment is that pressure in excess of 4 atmospheres. Together with the high pressure inflation capability, sufficient vacuum can be generated on the same device which facilitates rapid balloon deflation of a medical device.

Figure 8A:
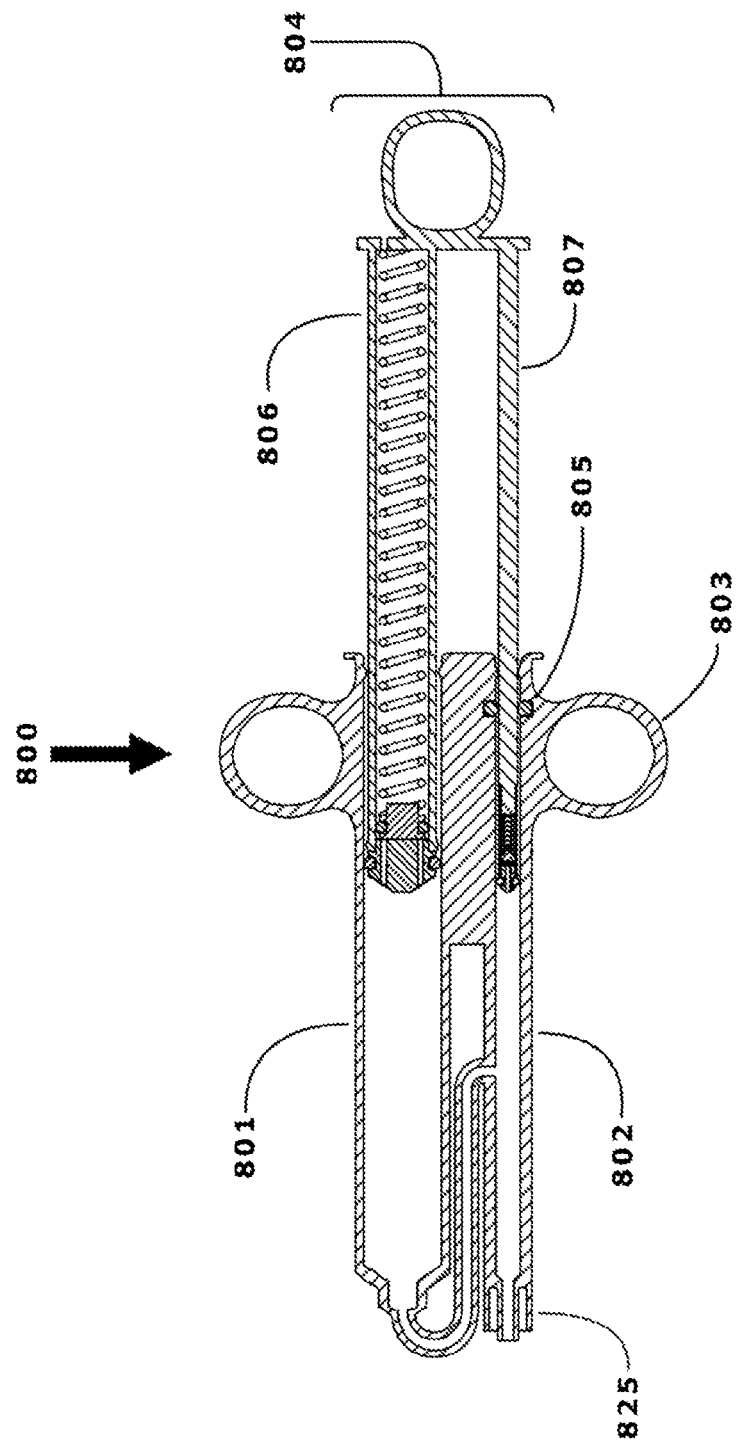
FIGS. 8A-8B depict cross-sectional views of an embodiment of the invention comprising a pressure limiting feature and a parallel deflation and inflation syringe arrangement.
Figure 8B:
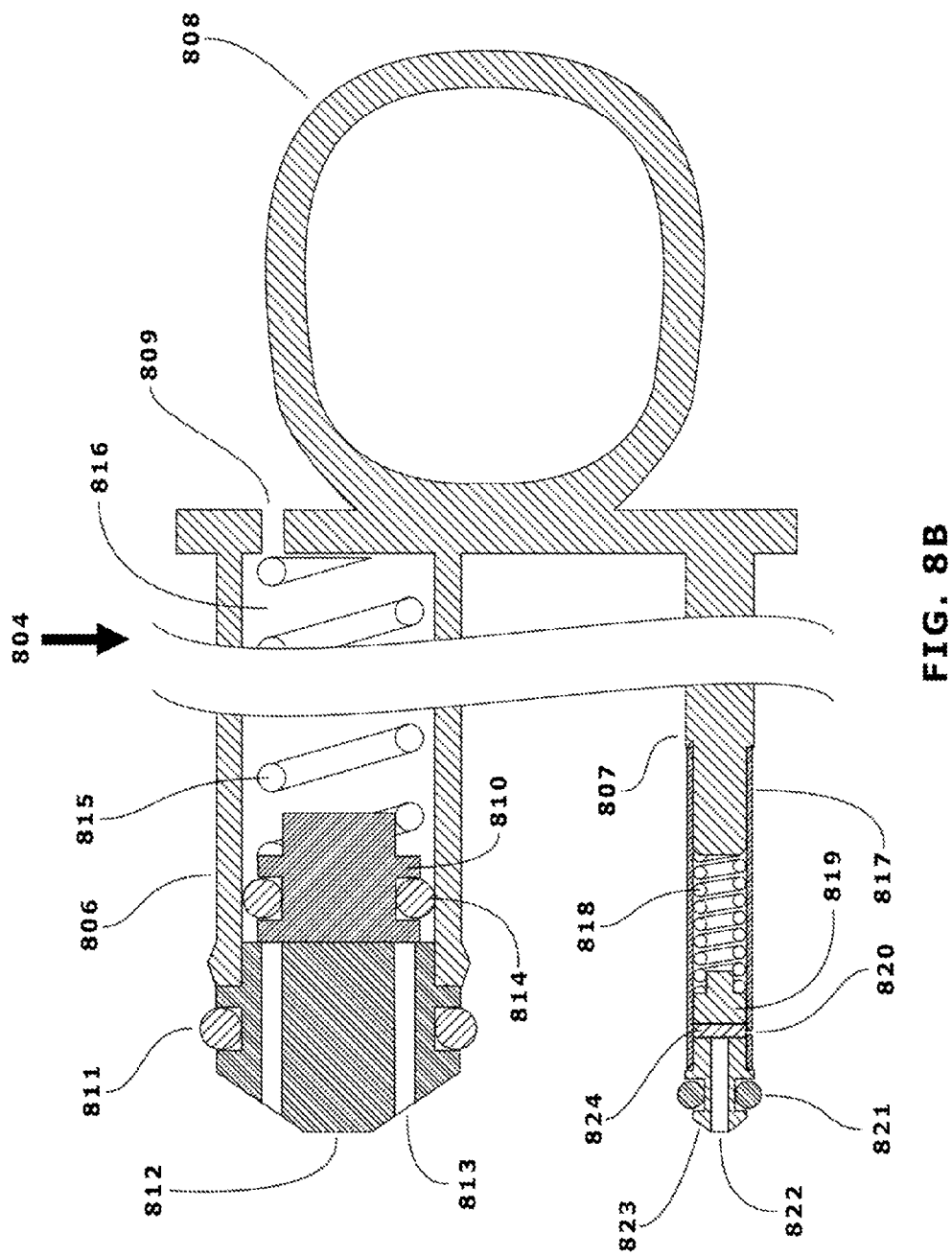

FIGS. 8A-8B illustrate another embodiment of the invention. Inflation/deflation syringe 800 is comprised of a deflation syringe 801, an inflation syringe 802, a plunger 804, inflation syringe seal 805, port connector 825, and at least one grip 803. The distal end of the deflation syringe 801 is connected to a port in the sidewall of inflation syringe 802. Deflation syringe 801 may be fabricated from materials known in the art including, but not limited to polycarbonate, polypropylene, polymethylmethacrylate, PET, PEEK, stainless steel, brass, aluminum, titanium, borosilicate glass, ceramics, and the like or combinations thereof, and may be transparent, translucent, opaque, or any gradient thereof. The inflation syringe 802 may be smaller (e.g. with a volume capacity of about 1 ml) than the deflation syringe 801 (e.g. with a volume capacity equal to or greater than 5 ml) and may be fabricated from materials known in the art including, but not limited to polycarbonate, polypropylene, polymethylmethacrylate, PET, PEEK, stainless steel, brass, aluminum, titanium, borosilicate glass, ceramics, and the like or combinations thereof, and may be transparent, translucent, opaque, or any gradient thereof. The inflation syringe 802 may be dimensioned to have a relatively small inner diameter and is used as the inflation chamber whereby the deflation syringe 801 may be dimensioned to have a larger inner diameter relative to inflation syringe 802 and is used as the deflation chamber as well as a reservoir for inflation media such as air or liquid. While grip 803 is shown as a ring, it should be obvious that other features that enable and/or ease handling of inflation/deflation syringe 800 may be freely interchanged with grip 803 including, but not limited to flanges, cantilevers, overmolded components of durometer different from that of deflation syringe 801 and inflation syringe 802, ridges, triggers, wings, and the like. Plunger 804 is sized such that deflation plunger 806 is coaxially disposed within deflation syringe 801 and inflation plunger 807 is coaxially disposed within inflation syringe 802. Port connector 825 may include but is not limited to fixed male or female luer lock fittings, rotating male or female luer lock fittings, hose barbs, slip luers, quick release fittings, and the like. In place of a port connector 825 provided at the distal end of the inflation syringe 802, an extension line or tubing (not shown) may be permanently attached to the distal end of the inflation siring 802 and the port connector 825 may attached to the distal end of the extension line (not shown).

As shown in FIG. 8B, plunger 804 comprises a deflation plunger 806, and inflation plunger 807, grip 808, and pressure release port 809. Deflation plunger 806 further comprises deflation plunger tip 812, deflation plunger tip port 813, deflation plunger seal 811, deflation plunger chamber 816, piston seal 814, piston 810, and piston return spring 815. Deflation plunger 806 is sized to fit coaxially within deflation syringe 801 and may be fabricated from materials known in the art including, but not limited to polycarbonate, polypropylene, polymethylmethacrylate, PET, PEEK, stainless steel, brass, aluminum, titanium, borosilicate glass, ceramics, and the like or combinations thereof, and may be transparent, translucent, opaque, or any gradient thereof. Deflation plunger tip 812 is joined to the distal end of deflation plunger 806 by methods known in the art including, but not limited to press fitting, adhesive bonding, ultrasonic welding, threading/tapping, overmolding, heat fusing, use of a set screw, and the like and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Furthermore, deflation plunger tip 812 and deflation plunger 806 may be integrated and made as single component by means of commonly known fabrication techniques such as machining, injection molding, blow molding, casting, and the like or combinations thereof. Deflation plunger tip 812 further comprises at least one deflation plunger tip port 813. Deflation plunger tip port 813 may be fabricated using methods known in the art including, but not limited to laser cutting and or engraving, mechanical machining, electrical discharge machining, chemical etching, and the like. Alternatively, deflation plunger tip port 820 may be formed in deflation plunger tip 812 as a feature of deflation plunger tip 812 during a molding process. Deflation plunger seal 811 is sized and arranged such that it provides an air and/or fluid tight seal between the deflation plunger tip 812 and the inner surface of deflation syringe 801 and may be fabricated from materials including, but not limited to polychloroprene, silicone rubber, nitrile rubber, Viton®, EPDM, butyl rubber, natural rubber, polyethylene, and the like. While deflation plunger seal 811 is depicted as an o-ring in FIG. 8B, it should be clear to those of skill in the art that equivalent components such as gaskets may be interchanged with deflation plunger seal 811. For example, deflation seal 811 may be an integral part of deflation plunger tip 812, such as one or more flanges molded, machined, or otherwise manufactured as a feature of deflation plunger 812 that provides an air and/or liquid tight seal between deflation plunger tip 812 and the inner surface of deflation syringe 801. Piston 810 coaxially resides within deflation plunger chamber 816 and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Piston 810 is biased by return spring 815 such that the distal face of piston 810 is positioned against the proximal face of deflation plunger tip 812. Piston seal 814 may be held within a feature such as a groove or channel on piston 810, and is sized such that it creates an air and/or liquid tight seal between piston 810 and the inner surface of deflation plunger 806 while allowing translation of piston 810 along deflation plunger chamber 816 and may be fabricated from materials including, but not limited to polychloroprene, silicone rubber, nitrile rubber, Viton®, EPDM, butyl rubber, natural rubber, polyethylene, and the like. While piston seal 814 is depicted as an o-ring in FIG. 8B, it should be clear to those of skill in the art that equivalent components such as gaskets may be interchanged with piston seal 814. For example, piston seal 814 may be an integral part of piston 810, such as one or more flanges molded, machined, or otherwise manufactured as a feature of piston 810 that provides an air and/or liquid tight seal between piston 810 and the inner surface of deflation plunger 806. Piston return spring 815 resides within deflation plunger chamber 816, and has a combination of spring rate, length, pitch, wire thickness, and outer diameter such that the distal end of piston return spring 815 places a compressive load against the piston 810. Piston return spring 815 may be fabricated from materials known in the art including but not limited to high carbon wire, alloy steel, stainless steel, nitinol, non-ferrous alloy, high-temperature alloy, and the like. Pressure release port 809 is provided to prevent pressure build up inside the deflation plunger chamber 816 when the piston 810 moves proximally.

Inflation plunger 807 further comprises inflation plunger tip 823, inflation plunger tip port 822, inflation plunger seal 821, inflation plunger housing 817, face seal 824, outlet port 820, pressure control spring 818, and pressure control piston 819. Inflation plunger housing 817 is joined to the distal end of inflation plunger 806 using methods known in the art including, but not limited to press fitting, adhesive bonding, ultrasonic welding, threading/tapping, overmolding, heat fusing, use of a set screw, and the like and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Alternatively, inflation plunger housing 817 and inflation plunger 806 may be machined, molded, or otherwise formed as a single integrated component. Inflation plunger housing 817 further comprises outlet port 820. Outlet port 820 may be fabricated using methods known in the art including but not limited to laser cutting and or engraving, mechanical machining, electrical discharge machining, chemical etching, and the like. Alternatively, outlet port 820 may be formed in inflation plunger housing 817 as a feature of inflation plunger housing 817 during a molding process. Inflation plunger tip 823 is joined to the distal end of inflation plunger housing 817 using methods known in the art including, but not limited to press fitting, adhesive bonding, ultrasonic welding, threading/tapping, overmolding, heat fusing, use of a set screw, and the like and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Inflation plunger tip 823 further comprises at least one inflation port 822 extending from the distal to proximal ends of inflation plunger tip 823, and may be fabricated using methods known in the art including, but not limited to laser cutting and or engraving, mechanical machining, electrical discharge machining, chemical etching, and the like. Alternatively, inflation port 822 may be formed in inflation plunger tip 823 as a feature of inflation plunger tip 823 during a molding process. Inflation plunger seal 821 may be held within a feature such as a groove or channel on inflation plunger tip 823, and is sized such that it creates an air and/or liquid tight seal between inflation plunger tip 823 and the inner surface of inflation syringe 802 and may be fabricated from materials including, but not limited to polychloroprene, silicone rubber, nitrile rubber, Viton®, EPDM, butyl rubber, natural rubber, polyethylene, and the like. While inflation plunger seal 821 is depicted as an o-ring in FIG. 8B, it should be clear to those of skill in the art that equivalent components such as gaskets may be interchanged with inflation plunger seal 821. For example, inflation plunger seal 821 may be an integral part of inflation plunger tip 823, such as one or more flanges molded, machined, or otherwise manufactured as a feature of inflation plunger tip 823 that provides an air and/or liquid tight seal between inflation plunger tip 823 and the inner surface of inflation syringe 802. Face seal 824 resides inside inflation plunger housing 817 and is sized to provide an air and/or fluid tight seal when pressed against the proximal end of the inflation plunger tip 823. Face seal 824 may be fabricated from materials known in the art including, but not limited to polychloroprene, silicone rubber, nitrile rubber, Viton®, EPDM, butyl rubber, natural rubber and the like. Pressure control piston 819 coaxially resides within inflation plunger housing 817 and may be fabricated from materials known in the art including, but not limited to polycarbonate, polypropylene, polymethylmethacrylate, polyurethane, nylon, Pebax, PET, PEEK, Delrin®, polychloroprene, silicone rubber, nitrile rubber, Viton®, EPDM, butyl rubber, natural rubber, PTFE, stainless steel, brass, aluminum, titanium, borosilicate glass, ceramics, and the like or combinations thereof. Pressure control piston 819 is biased by pressure control spring 818 such that the distal face of pressure control piston 819 contacts the proximal surface of face seal 824. Pressure control piston 819 may be joined to face seal 824 or the two components may be decoupled from each other. Methods of joining the two components may comprise, but are not limited to press fitting, adhesive bonding, ultrasonic welding, threading/tapping, overmolding, use of a set screw, and the like. Alternatively, pressure control piston 819 and face seal 824 may be manufactured as a single unit. The proximal end of pressure control piston 819 serves as a base to stabilize the distal end of pressure control spring 818. Pressure control spring 818 resides within inflation plunger housing 817 such that the distal end of pressure control spring 818 places a compressive load on pressure control piston 819. Pressure control piston 819 transmits at least some of the compressive load applied by pressure control spring 818 to the proximal surface of face seal 824, thus maintaining a seal between inflation plunger tip 823 and the distal surface of face seal 824. Pressure control spring 818 maintains this seal until a desired pressure is exceeded; this pressure is dictated by the force (or spring force constant) of pressure control spring 818 at a given length of compression by specifying the overall length, pitch, wire thickness, wire material and outer diameter of pressure control spring 818. Pressure control spring 818 may be fabricated from materials known in the art including, but not limited to high carbon wire, alloy steel, stainless steel, nitinol, non-ferrous alloy, high-temperature alloy, and the like.

While grip 808 is shown as a ring, it should be obvious that other features that enable and/or ease handling of inflation/deflation syringe 800 may be freely interchanged with grip 808 including, but not limited to flanges, cantilevers, overmolded components of durometer different from that of plunger 804, ridges, triggers, wings, and the like that may be used by the operator to allow the inflation/deflation syringe 800 to be held with a single hand and provide stability when advancing or retracting the plunger 804.

The pressure control mechanism of the embodiment of the invention shown in FIGS. 8A and 8B provides the same function as that described in FIGS. 3A and 3B. Similarly, while the pressure control mechanism has been depicted as a spring and seal combination in this embodiment, other valve and/or seal mechanisms including but not limited to ball valves, duckbill valves, umbrella valves, check valves, diaphragms, shuttling valves, flap valves and the like may be incorporated into the mechanism.

The design of the inflation/deflation syringe 800 allows inflation media inside the deflation syringe 801 to be displaced and transferred to the deflation plunger chamber 816. As plunger 804 translates distally and the pressure within deflation syringe 801 exceeds a pre-set value, the piston 810 and piston seal 814 assembly is pushed back proximally and the inflation media is directed through deflation plunger tip port 813 and into deflation plunger chamber 816. The piston 810 and piston seal 814 assembly provides a leak free seal that keeps the inflation fluid inside the deflation plunger chamber 816. When the plunger 804 is retracted for deflation the inflation media inside the deflation plunger chamber 816 is returned to deflation syringe 801 through deflation plunger tip port 813. The retraction of syringe plunger 804 creates a negative pressure inside the deflation syringe 801. The negative pressure (with respect to the ambient pressure on the proximal side of the piston 810 and piston seal 814) draws the inflation media into deflation syringe 801 and pulls the piston 810 and piston seal 814 assembly distally within the deflation plunger chamber 816. The piston return spring 815 maintains the piston 810 in a normally biased position against the proximal face of deflation plunger tip 812 when the pressure in deflation syringe 801 is less than that applied by the piston return spring 815 to the piston 810.

Alternatively (not shown), deflation plunger seal 811 and inflation plunger seal 821 may reside on a channel, groove, or similar feature of deflation syringe 801 and inflation syringe 802, respectively, that allows for hermetic seals between deflation syringe 801 and deflation plunger 806, and inflation syringe 802 and inflation plunger 807. In this embodiment, the outlet port 820 is positioned or located proximal of the inflation plunger seal 821 when the plunger 804 is fully depressed into deflation syringe 801 and inflation syringe 802. The outlet port 820 may be incorporated to the inflation rod 807 by way of providing an inner lumen or opening (not shown) through the length of inflation rod 807 originating from the distal end and terminating at the proximal end of the inflation rod 807. Alternatively, the location of inflation plunger housing 817, face seal 824, pressure control spring 818, and pressure control piston 819, may be positioned proximally (not shown) by increasing the length of the inflation plunger tip 823 and decreasing the length of the inflation rod 807, thus shifting the outlet port 820 proximal of the inflation plunger seal 821 when the plunger 804 is fully depressed into deflation syringe 801 and inflation syringe 802.

Figure 9A:
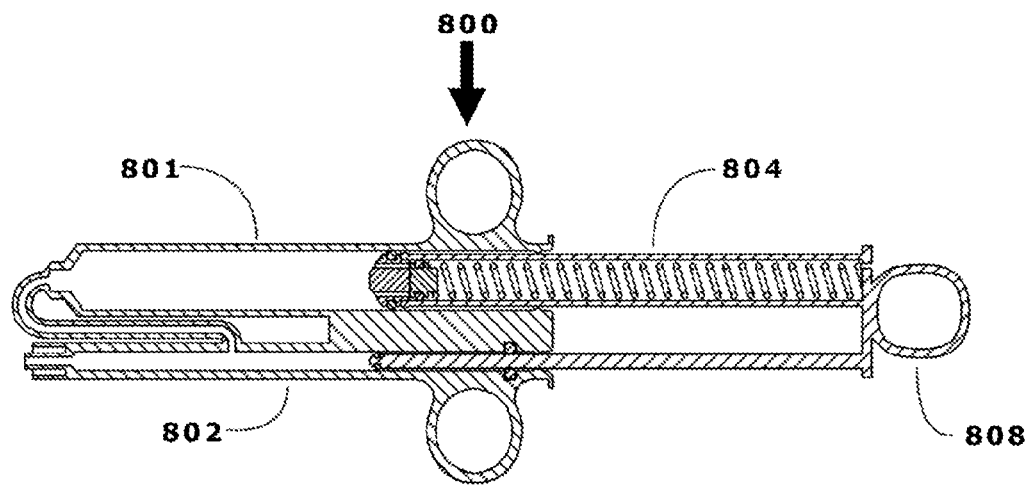
FIG. 9A-9C depict a method of operation of the embodiment of the invention illustrated in FIGS. 8A-8B.
Figure 9B:
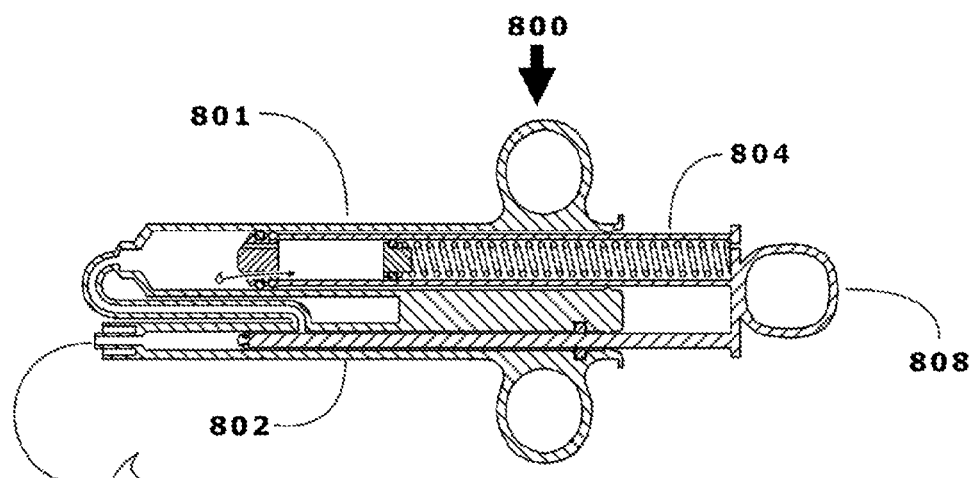
Figure 9C:
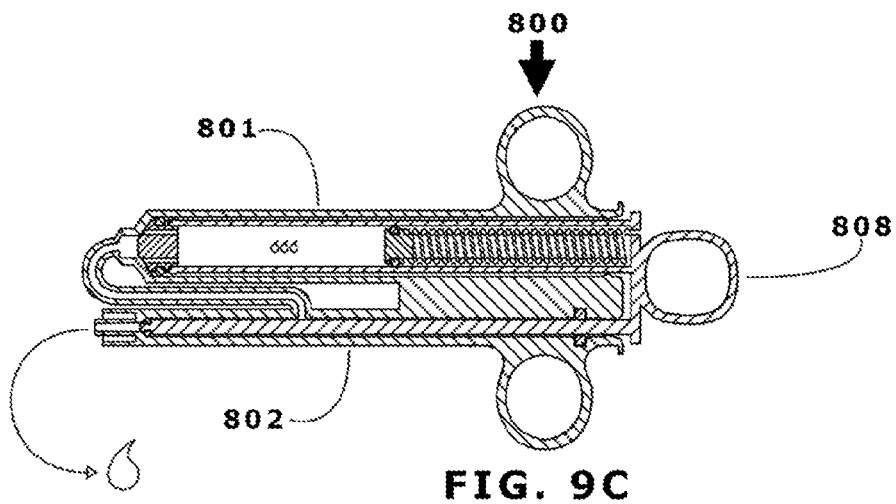

FIG. 9A-9C illustrate a method of the using one embodiment of the inflation/deflation syringe of the invention. The inflation/deflation syringe 800 can be used to inflate and deflate an inflatable element (not shown) of a medical device such as balloon catheter (not shown) and the like. FIG. 9A shows the relative position of the elements of the components of the invention when inflation media has been fully drawn into the deflation syringe 801 and inflation syringe 802. Excess inflation media and/or air or air bubbles above the media level inside the deflation syringe 801 and inflation syringe 802 can be purged out by advancing the plunger 804, while the syringe 800 is held vertically. A visual indicator (not shown) such as printed markers or the like, or a tactile indicator such as detents or the like, may be incorporated into the inflation/deflation syringe 800 to aid the user in filling the lumens of the deflation syringe 801 and/or inflation syringe 802 with the proper amount or volume of inflation media. The port connector 825 may then be attached to the medical device inflation port. Alternatively, an inflation line extension (not shown) may be attached to the port connector 825 prior to purging the excess inflation media. Once the inflation line extension is connected, excess inflation media and/or air or air bubbles above the fluid level inside the deflation syringe 801 and inflation syringe 802 can be purged out by advancing the plunger 804, while the syringe 800 is held vertically. At this point, the inflation line lumen (not shown) should be filled with inflation media and the distal end of the extension line can be attached to a medical device such as a balloon catheter, for example. A balloon catheter, for example, may be prepared by aspirating the air out of the balloon inflation path by fully retracting the plunger 804 and allowing the air/air bubbles to be purged out (not shown). This is done by holding the syringe 800 such that the distal tip is pointed down prior to retracting the plunger 804 and then releasing to neutral. FIGS. 8B and 8C show the subsequent one-handed inflation of the balloon catheter. The user may advance grip 808 distally until the plunger 804 is at the end of the advancement stroke. The balloon may then be deflated by fully retracting the plunger 804. Once the balloon of the medical device is deflated, grip 808 can be released return plunger 804 to a neutral (equilibrated pressure) position.

In yet another embodiment of inflation/deflation syringe 800, the pressure control mechanism comprised of the face seal 820, pressure control piston 819, pressure control spring 818, along with the associated components such as inflation plunger tip port 822, inflation plunger housing 817 and outlet port 820 can be eliminated and replaced with a standard inflation plunger (not shown) and seal 821 configuration. In this configuration, the internal pressure generated inside the inflation syringe 802 is not limited. However, this internal pressure can be monitored by adding a pressure gage or indicator or sensor with indicator (not shown) at the distal end of the syringe body where it is in communication with the inflation fluid path. The pressure gage or indicator set up is typically seen on standard inflation devices as described earlier. The difference between the device described in this invention and that of a typical inflation device is the ability of the user to use a single hand to generate very high pressure inflation in a controlled manner. Very high inflation pressure as defined in this embodiment is that pressure in excess of 4 atmospheres. Together with the high pressure inflation capability, sufficient vacuum can be generated on the same device which facilitates rapid balloon deflation of a medical device.

Furthermore (not shown), the inflation/deflation syringes 100, 600, and 800 may comprise locking mechanisms known in the art that can be engaged or disengaged, such as those taught in U.S. Pat. No. 5,215,536 and herein incorporated in full by reference, between the syringe plungers and syringe barrels that allow or enable a desired pressure or vacuum to be maintained within inflation/deflation syringes 100, 600, and 800.

In yet another embodiment of this invention, inflation/deflation syringes 100, 600, and 800 may be used to deliver a low volume of inflation media in a controlled manner. This may have application in the inflation of a low pressure balloon, for example. In this use, a graduation or marking on the syringe body may be aligned with a feature on the inflation and/or deflation plungers to signal the delivery of an appropriate volume of inflation media.

The preceding merely illustrates the principles of the invention. It will be appreciated that those skilled in the art will be able to devise various arrangements, which, although not explicitly described or shown herein, embody the principles of the invention, and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An inflation/deflation syringe that generates pressure or delivers a controlled volume, comprising:
    a syringe barrel comprising a first smaller diameter chamber and an adjacent second larger diameter chamber;
    a syringe plunger comprising multiple diameters sized to fit within the syringe barrel, wherein a syringe plunger segment of large diameter is hollow and in fluid communication with the second larger diameter chamber of the syringe barrel and an adjacent fixed syringe plunger segment of small diameter comprising a solid rod sized to fit within the first smaller diameter chamber of the syringe barrel; and
    a piston and/or seal disposed and hermetically sealed within an inner chamber of the syringe plunger segment of large diameter, and
    wherein the multiple chambers of the syringe barrel are in fluid communication with one another when the syringe plunger is fully retracted within the syringe barrel.

2. The inflation/deflation syringe of claim 1, wherein all chambers of the syringe barrel are directly connected in serial and/or parallel arrangements.

3. The inflation/deflation syringe of claim 1, wherein the first smaller diameter chamber and the second larger diameter chamber of the syringe barrel are in parallel arrangement.

4. The inflation/deflation syringe of claim 1, wherein the small diameter syringe plunger segment is directly connected to and in serial or parallel arrangement with the large syringe plunger segment.

5. The inflation/deflation syringe of claim 1, wherein each syringe plunger segment comprises a sealing member.

6. The inflation/deflation syringe of claim 5, wherein the sealing member is located at the distal end of each syringe plunger segment.

7. The inflation/deflation syringe of claim 1, wherein each syringe barrel chamber comprises a sealing member.

8. The inflation/deflation syringe of claim 1, wherein the small diameter syringe plunger segment further comprises a pressure regulating or limiting mechanism.

9. The inflation/deflation syringe of claim 1, wherein a pressure gage or pressure monitoring indicator is connected to the first smaller diameter chamber of the syringe barrel.

10. The inflation/deflation syringe of claim 1, wherein the first smaller diameter chamber of the syringe barrel chamber in conjunction with the syringe plunger segment of small diameter provides high pressure inflation or controlled volume delivery.

11. The inflation/deflation syringe of claim 1, wherein the second larger diameter chamber of the syringe barrel chamber provides vacuum and/or a reservoir for an inflation media.

12. The inflation/deflation syringe of claim 11, further comprising a media release port in large diameter syringe plunger segment.

13. The inflation/deflation syringe of claim 11, wherein the inflation media is gas and/or liquid.

14. The inflation/deflation syringe of claim 1, wherein high pressure inflation or a controlled volume delivery can be generated using a single hand and the syringe plunger can be retracted post inflation or post controlled volume delivery using a single hand.

15. The inflation/deflation syringe of claim 1, wherein the inflation/deflation syringe may be locked to maintain a desired inflation pressure.

16. The inflation/deflation syringe of claim 1, wherein the inflation/deflation syringe may be locked to maintain a desired deflation pressure or vacuum.

17. The inflation/deflation syringe of claim 1, wherein the piston and/or seal disposed and hermetically sealed within the inner chamber of the syringe plunger of large diameter is biased towards the distal end of the inner chamber of the syringe plunger of large diameter under neutral pressure.

18. The inflation/deflation syringe of claim 1, further comprising at least one marker to indicate a desired fill volume of inflation media.

19. A method of using the inflation/deflation syringes of claim 1, comprising;
    drawing inflation media into the syringe barrel chambers;
    expelling excess gas and/or inflation media from the syringe barrel chambers;
    connecting to the inflation port of a medical device;
    transferring inflation media into the medical device to a desired pressure and/or volume, and
    withdrawing inflation media from the medical device when desired to return the pressure and/or volume of the inflation media within the medical device to a desired level.

20. The method of claim 19, wherein the volume of inflation media drawn into the inflation/deflation syringe does not exceed the volume of the larger diameter syringe barrel.

21. The method of claim 19, wherein the inflation/deflation syringe is filled with a desired volume of inflation media using visual markers or tactile feedback.

22. The method of claim 19, wherein the inflation/deflation syringe is locked in position after transferring inflation media into the medical device to maintain the desired pressure and/or volume of media in the medical device.

23. The method of claim 19, wherein the inflation/deflation syringe is locked in position after withdrawing inflation media from the medical device to attain a desired pressure and/or volume of media in the medical device.

* * * * *